(12) United States Patent
Sardashti et al.

(10) Patent No.: US 7,876,425 B2
(45) Date of Patent: Jan. 25, 2011

(54) METHOD AND APPARATUS FOR SURFACE ENHANCED RAMAN SPECTROSCOPY

(75) Inventors: Maziar Sardashti, Bartlesville, OK (US); Raul J. Barriga, Lake Jackson, TX (US); David J. Blumer, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 339 days.

(21) Appl. No.: 12/047,141

(22) Filed: Mar. 12, 2008

(65) Prior Publication Data

US 2009/0231577 A1 Sep. 17, 2009

(51) Int. Cl.
*G01J 3/44* (2006.01)
*G01N 21/65* (2006.01)
*G01N 21/01* (2006.01)

(52) U.S. Cl. .................. 356/72; 356/301; 356/246
(58) Field of Classification Search .................. 356/72, 356/246
See application file for complete search history.

(56) References Cited

U.S. PATENT DOCUMENTS

| | | | |
|---|---|---|---|
| 4,142,802 A * | 3/1979 | Pollak et al. ........... | 356/319 |
| 5,255,067 A | 10/1993 | Carrabba et al. | |
| 5,693,152 A | 12/1997 | Carron | |
| 6,015,479 A * | 1/2000 | Boss et al. ........... | 204/412 |
| 6,028,667 A | 2/2000 | Smith et al. | |

FOREIGN PATENT DOCUMENTS

| WO | WO 2004/011145 | 2/2004 |
|---|---|---|
| WO | WO 2006/137885 | 12/2006 |

OTHER PUBLICATIONS

Brown et al: SERS study of the interaction of thiourea with a copper electrode in sulphuric acid solution, Journal of Electroanalytical Chemistry, vol. 380, Jan. 1995, pp. 161-166.*
Simard et al: In situ micro-Raman spectroscopy to investigate pitting corrosion of 1024 mild steel in phosphate and bicarbonate solutions containing chloride and sulfuric ions, Journal of Applied Electrochemistry, vol. 31, 2001, pp. 913-920.*
Durnie et al: In situ SERS study of adsorption of inhibitors of carbon dioxide corrosion, Surface and Interface Analysis, vol. 35, 2003, pp. 536-543.*
Raman Technical Resources—Raman Tutorial; Kaiser Optical Systems, Inc. A Rockwell Collins Company; http://www.kosi.com/raman/resources/tutorial/; Sep. 4, 2007; pp. 1-5.

* cited by examiner

*Primary Examiner*—F. L Evans

(57) ABSTRACT

A test cell comprises a test chamber at least partially enclosed by a wall. The test chamber holds a test fluid, and a test material is placed within the test chamber such that at least a portion of the test material is contact with the test fluid and at least a portion of the test material is in optical register with a window of the wall. A first conductive element is in electrical communication with the test fluid but is separated from the test material by a space, and extends to an outside of the cell. A second conductive element is in electrical communication with the test material and also extends to the outside of the cell.

24 Claims, 4 Drawing Sheets

METHOD AND APPARATUS FOR SURFACE ENHANCED RAMAN SPECTROSCOPY

BACKGROUND

1. Field

The present technology relates to systems and methods for spectroscopy analysis. More particularly, embodiments of the technology involve a system and method for performing surface enhanced Raman spectroscopy.

2. Related Art

Surface Enhanced Raman Spectroscopy (SERS), or scattering, is a technique for analyzing a material to identify components of the material present at a surface of the material and other materials that have come in contact with the surface. SIRS involves exposing the material under test to a monochromatic light source (such as a laser) and sensing the light reflected by the material under test. Characteristics of the reflected light provide a "fingerprint" of the material, including information about components present in the material. SERS can be used, for example, to detect and analyze corrosion taking place at the surface of a metal. This may be useful in evaluating the effectiveness of corrosion inhibiting agents.

Conventional SERS processes involve aligning a light source, such as a laser, with a material to be tested and aligning various light sensors with the material to be tested to capture the light reflected off the material. Aligning the emitter and the sensors for the conventional SERS processes is an iterative process that can take several hours to perform making the process inefficient at best.

Thus, there is a need for an improved SERS process that does not suffer from the limitations of conventional SERS processes.

SUMMARY

Embodiments of the present invention address the above-mentioned limitations and provide a distinct advance in the art of.

According to a first embodiment of the invention, a test cell comprises a test chamber at least partially enclosed by a wall, the wall including a window. The test cell further comprises a test fluid within the test chamber, and a test material within the test chamber, at least a portion of the test material in contact with the test fluid and at least a portion of the test material in optical register with the window. The test cell further comprises a first conductive element in electrical communication with the test fluid and separated from the test material by a space, the first conductive clement extending to an outside of the cell, and a second conductive element in electrical communication with the test material and extending to the outside of the cell.

According to a second embodiment of the invention, a test cell with an internal test chamber separated from an outside of the cell by a wall comprises a top planar segment of the wall including a substantially transparent portion, a test fluid within the test chamber, and a test material within the test chamber and immersed in the test fluid, the test material partially coated with an electrically insulating material such that only a single exposed face of the test material is in contact with the test fluid, wherein the exposed face is in optical register with the substantially transparent portion of the wall. The test cell further comprises a first conductive element in electrical communication with the test fluid and extending to the outside of the cell, a second conductive element with a first end in contact with the test fluid and a second end extending to the outside of the cell. The first end of the second conductive element is separated from the test material by a space, and the second conductive element is covered with an electrically insulating material preventing the second conductive element from contacting the test fluid. A third conductive element is in electrical communication with the test material and extends to the outside of the cell.

According to a third embodiment of the invention, a method of performing a spectroscopy analysis comprises adding a test fluid to an internal chamber of a cell; placing a test material in the cell such that the test material is at least partially in contact with the test fluid; aligning a substantially transparent portion of the cell with an optical component of a spectroscopy instrument; and performing the spectroscopy analysis on the test material by exposing the test material to light generated by the emitter and capturing light reflected from the test material using the optical component.

According to a fourth embodiment of the invention, a method of performing a spectroscopy analysis comprises adding a test fluid to an internal chamber of a cell; placing a test material in the cell such that the test material is submersed in the test fluid, the test material including a first conductive element extending to an outside of the cell, wherein the first conductive element and the test material are coated with an electrical insulating material such that only a single face of the test material is exposed to the test fluid; aligning said test material with a substantially transparent portion of said cell; aligning said substantially transparent portion of said cell with an optical component of a spectroscopy instrument, said optical component including a light emitter and a light sensor; applying an electric potential between said test material and a second conductive element, said second conductive element being in contact with said test fluid and separated from said test material by a space; and performing said spectroscopy analysis on said test material by exposing said test material to light generated by said emitter and capturing light reflected from said test material using said optical component.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the preferred embodiments and the accompanying drawing figures.

BRIEF DESCRIPTION OF THE DRAWING FIGURES

A preferred embodiment of the present technology is described in detail below with reference to the attached drawing figures, wherein.

Figure 1:
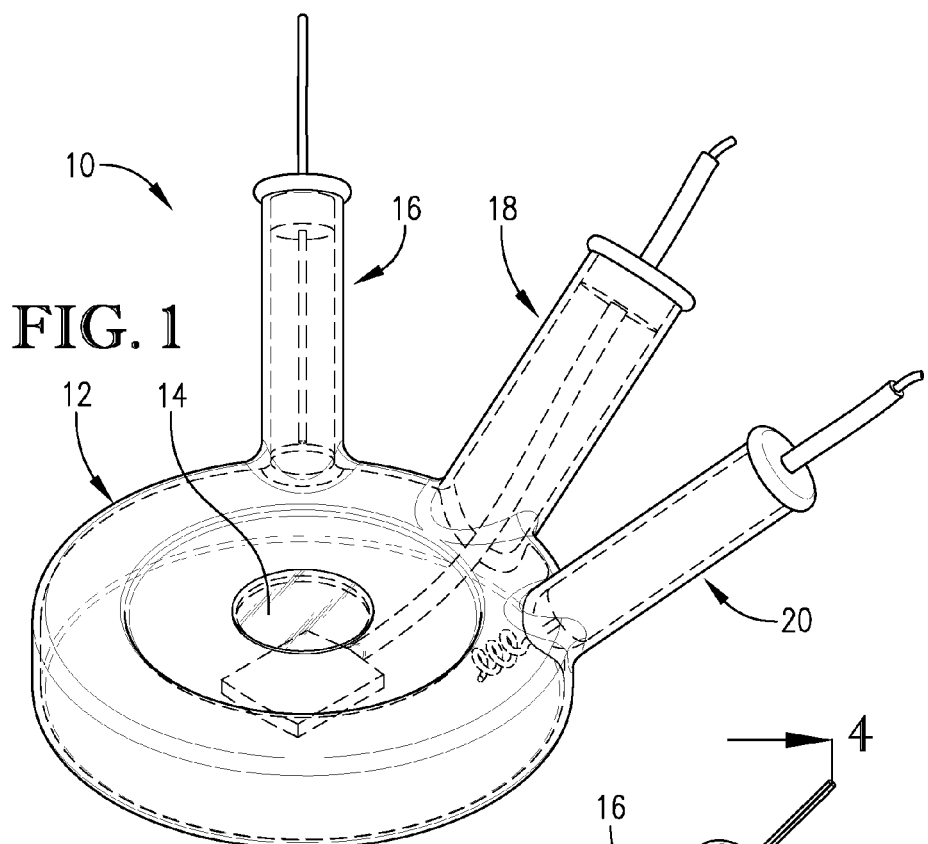
FIG. 1 is a perspective view of a test cell constructed according to principles of the present teachings and illustrating a test material placed within the cell.
Figure 2:
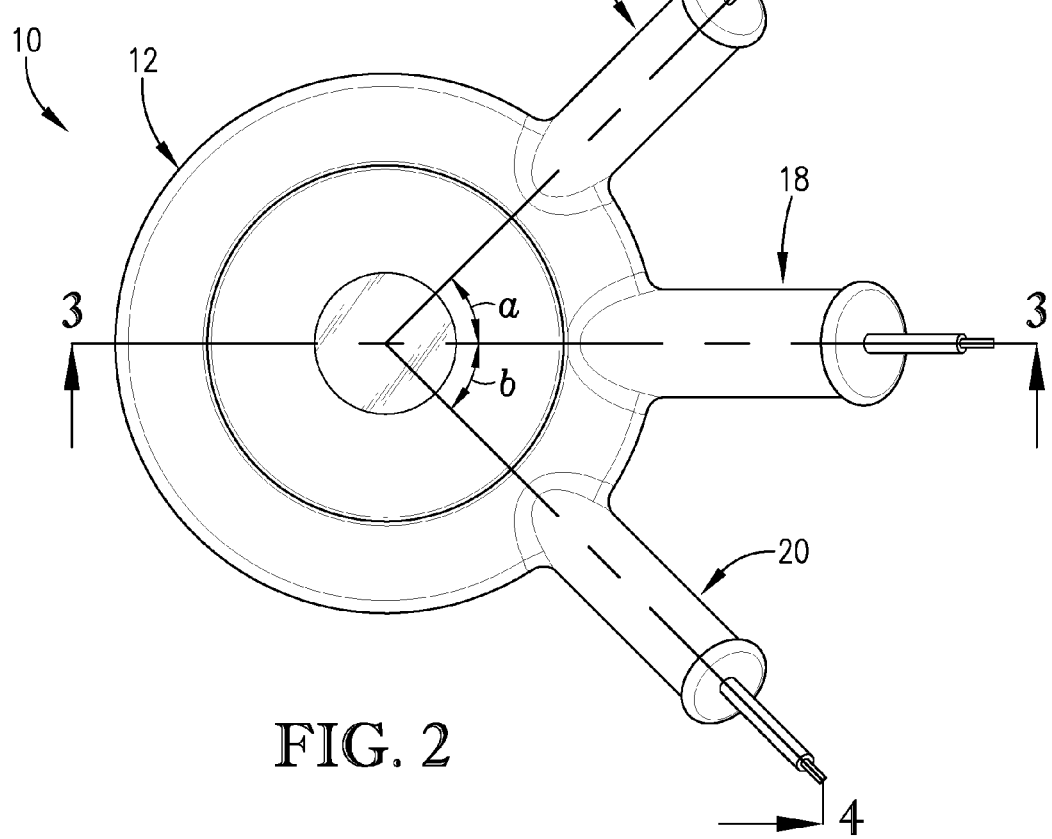
FIG. 2 is a plan view of the cell of FIG. 1.
Figure 3:
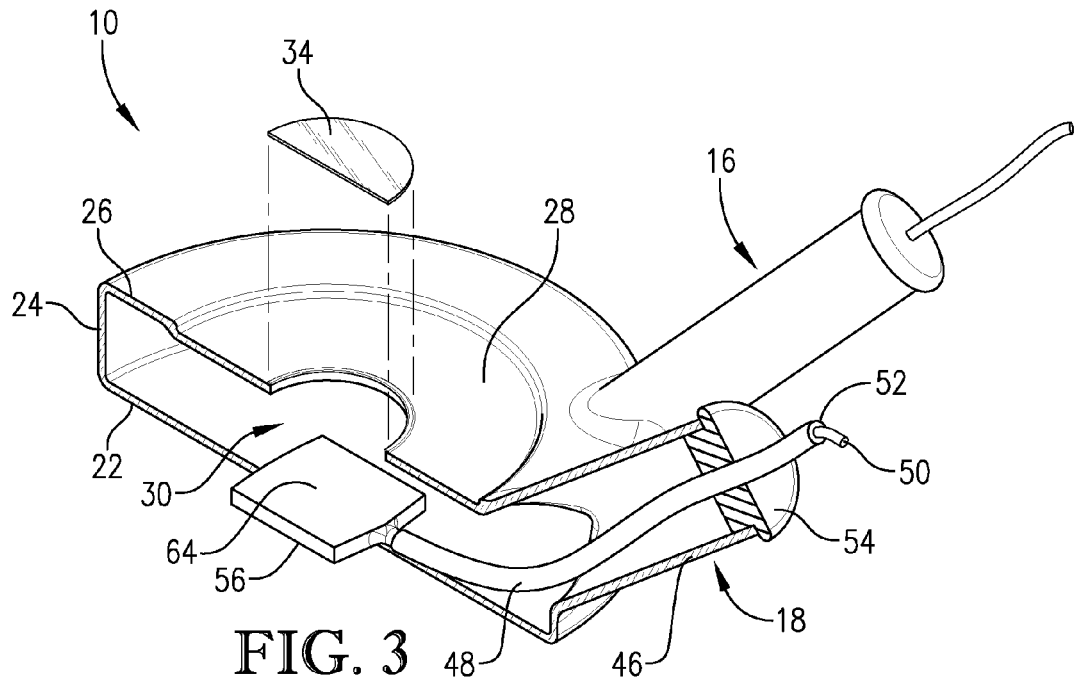
FIG. 3 is a cross-sectional view of the cell of FIG. 1 taken along line 3-3 of FIG. 2.
Figure 4:
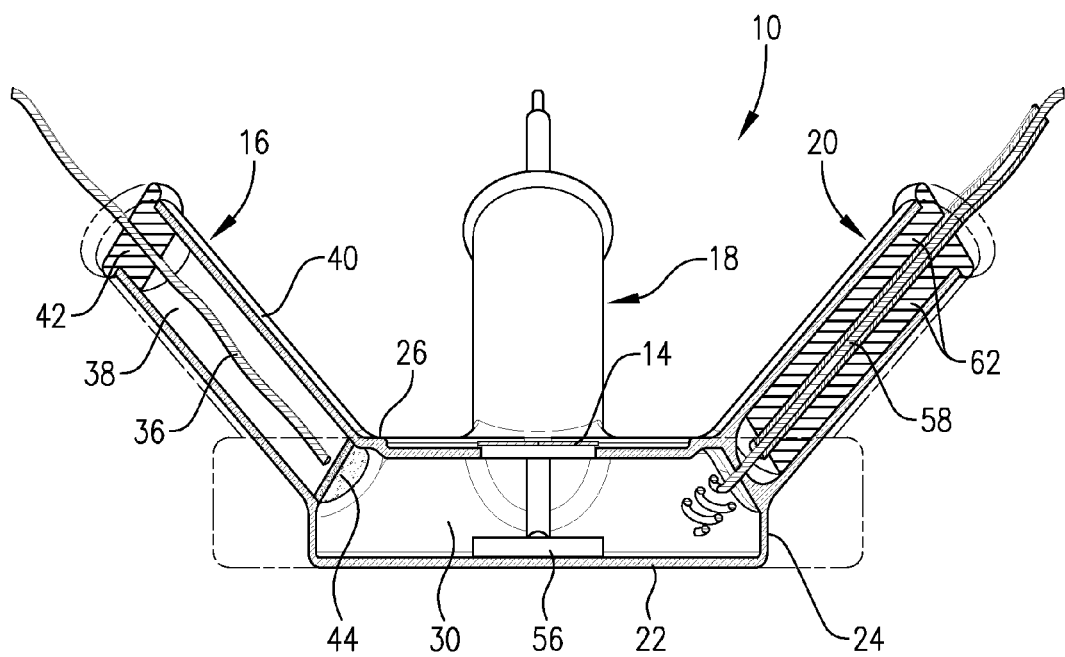
FIG. 4 is a cross-sectional view of the cell of FIG. 1 taken along line 4-4 of FIG. 2.
Figure 5:
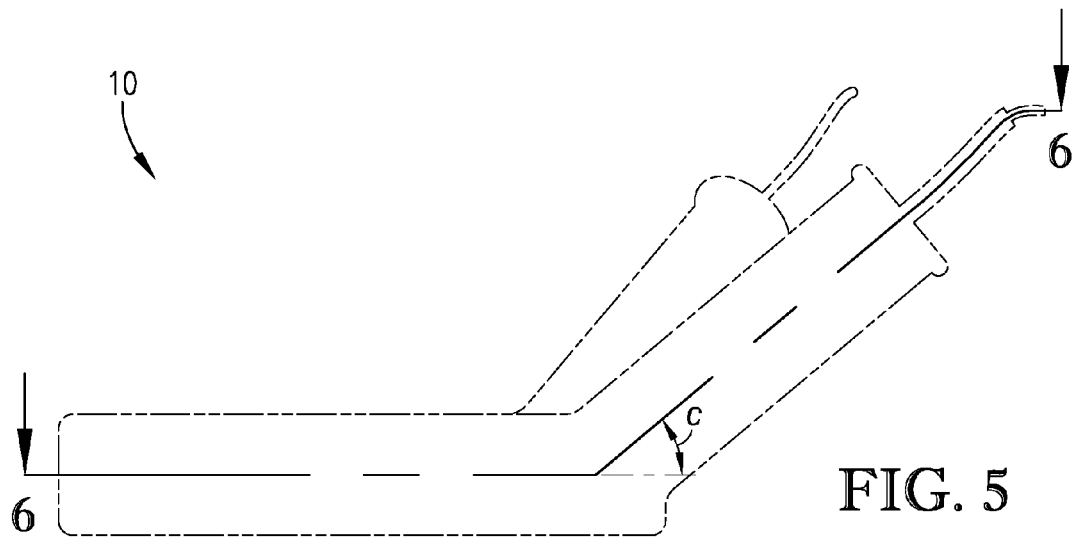
FIG. 5 is a side elevation view of the cell of FIG. 1 illustrating a perspective of FIG. 6.
Figure 6:
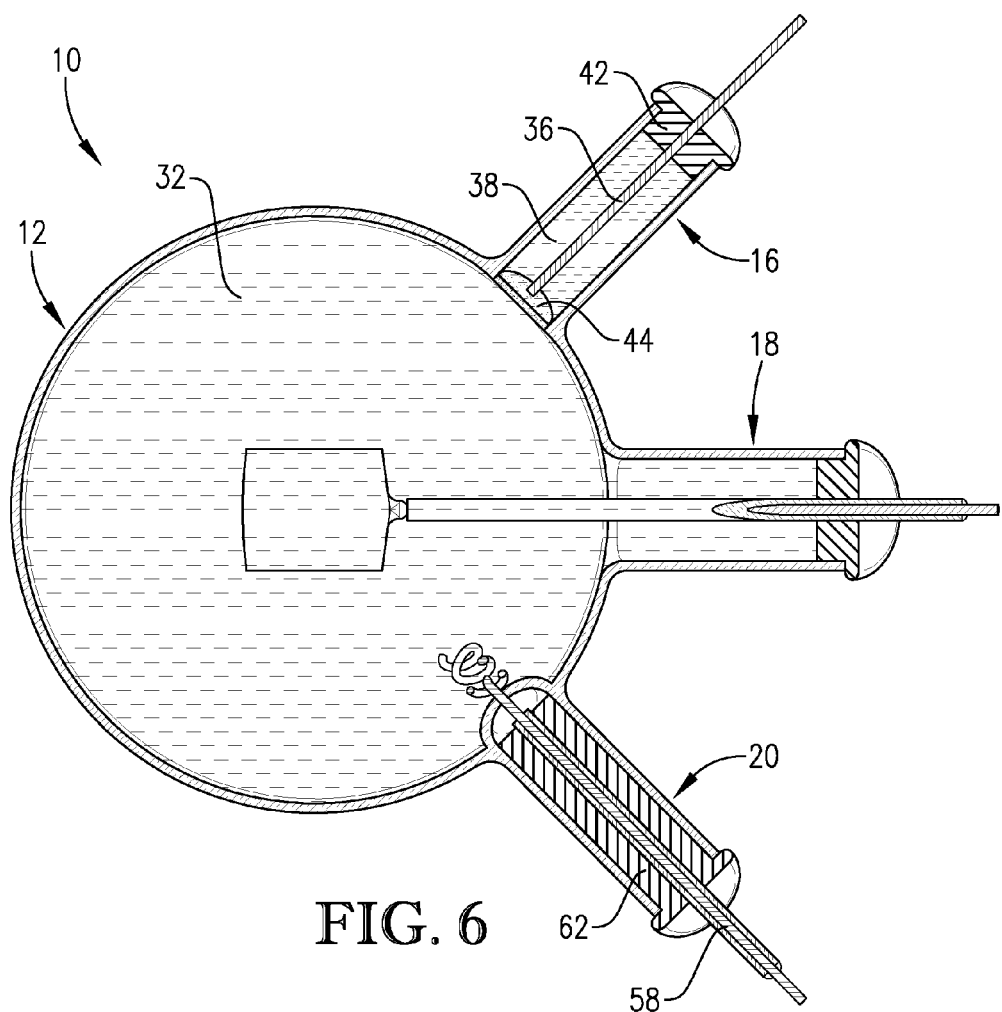
FIG. 6 is a cross-sectional view of the cell of FIG. 1 taken along line 6-6 of FIG. 5.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the present technology references the accompanying drawings that illustrate specific embodiments in which the technology may be practiced. The embodiments are intended to describe aspects of the technology in sufficient detail to enable those skilled in the art to practice the invention. Other embodiments can be utilized and changes can be made without departing from the scope of the present teachings. The following detailed description is, therefore, not to be taken in a limiting sense. The scope of the present invention is defined only by the appended claims, along with the full scope of equivalents to which such claims are entitled.

A test cell is illustrated in FIGS. 1-6 and designated generally by the reference numeral 10. The cell 10 may be used in spectroscopy analyses, including SERS, and generally includes a cell body 12 with a window 14, a first electrode tube 16, a second electrode tube 18, and a third electrode tube 20.

The body 12 may be cylindrical in shape (as illustrated), comprising a circular bottom wall 22, an annular side wall 24, and a circular top wall 26. The top wall 26 presents a recessed portion 28 that includes the window 14. The bottom wall 22, side wall 24, and top wall 26 may form a single, integral wall that defines an internal test chamber 30 that is adapted to hold a test fluid 32, explained below in greater detail. The walls 22,24,26 may be constructed of substantially any suitably durable material including glass, plastic, metal, or the like. Constructing the walls 22,24,26 of a substantially transparent material may be desirable to enable a user to view the contents of the cell 10 from various angles. In a particular embodiment, the walls 22,24,26 are constructed of PYREX.

While the body 12 is illustrated and described as being generally cylindrical in shape, embodiments of the invention may present other, equally-preferred shapes without departing from the spirit or scope of the present teachings. By way of example, the body 12 may present a rectangular, ovular, or arbitrary shape.

The recessed portion 28 is a generally planar region of the top wall 26 surrounding and including the window 14. While the recessed portion 28 is illustrated as presenting a circular pattern, the present teachings are not so limited and the recessed portion 28 may present other, equally-preferred patterns including, for example, rectangular patterns or arbitrarily-shaped patterns. The recessed portion 28 is generally parallel with the non-recessed portion of the top wall 26, though offset by a distance within the range of from about 0.5 mm to about 3.5 mm or within the range of from about 1.0 mm to about 3.0 mm. More particularly, the recessed portion 28 may be offset from the non-recessed portion of the top wall 26 a distance of about 1.5 mm, about 2.0 mm, or about 2.5 mm. The recessed portion 28 may be useful, for example, to facilitate spectroscopy analysis by accommodating placement of an optical component proximate the window 14.

The window 14 is a region that allows light to pass therethrough with minimal scattering, and thus is transparent or substantially transparent. The window may be an uncovered aperture in the top wall 26, or may include a thin plate or sheet of transparent material separating the test chamber 30 from outside the cell 10. By way of example, the window 14 may include a hole in the top wall 26 and a thin sheet of transparent material 34, such as a thin sheet of glass or plastic similar to a microscope slide cover, secured to a top or outer surface of the top wall 26. The thin sheet of transparent material 34 may be separate from the top wall 26 and secured thereto using an adhesive, such as a resin. Alternatively, the thin sheet of transparent material 34 may be an integral part of the top wall 26. The sheet of transparent material 34 may be substantially thinner than the wall 26, as explained below in greater detail.

The window 14 may be circular (as illustrated) and may have a diameter within the range of from about 0.5 cm to about 2.5 cm or within the range of from about 1.0 cm to about 2.0 cm. More particularly, the diameter of the window 14 may be about 1.3 cm, about 1.5 cm, or about 1.7 cm. The window 14 need not be circular but may present other shapes, including, for example, rectangular and triangular shapes. Regardless of the particular shape of the window 14, it may present an area within the range of from about $0.10$ $cm^2$ to about $5.0$ $cm^2$ or within the range of from about $1.0$ $cm^2$ to about $4.0$ $cm^2$. More particularly, the are of the window may be about $1.5$ $cm^2$ about $2.0$ $cm^2$, about $2.5$ $cm^2$, about $3.0$ $cm^2$, or about $3.5$ $cm^2$.

The bottom wall 22, side wall 24, and top wall 26 may each present a thickness within the range of from about 0.3 mm to about 1.7 mm, within the range of from about 0.5 mm to about 1.5 mm, or within the range of from about 0.7 mm to about 1.3 mm. More particularly, the bottom wall 22, side wall 24, and top wall 26 may each present a thickness of about 0.9 mm, about 1.0 mm, or about 1.1 mm. The window 14 may present a thickness within the range of from about 0.1 mm to about 0.3 mm or from about 0.15 mm to about 0.25 mm. More particularly, the window 14 may be about 0.17 mm thick, about 0.20 mm thick, or about 0.23 mm thick.

A diameter of the annular side wall 24 may be within the range of from about 2.0 cm to about 10.0 cm, within the range of from about 4.0 cm to about 8.0 cm, or within the range of from about 5.0 cm to about 7.0 cm. More particularly, the diameter of the annular wall 24 may be about 5.7 cm, about 6.0 cm, or about 6.3 cm. A volume of the test chamber 30 may be within the range of from about 20 $cm^3$ to about 60 $cm^3$ or from about 30 $cm^3$ to about 50 $cm^3$. More particularly, the volume of the test chamber 30 may be about 35 $cm^3$, about 40 $cm^3$, or about 45 $cm^3$.

The first electrode tube 16 houses a reference electrode including a conductive element 36 and a reference fluid 38. An outer tubular wall 40 and an end cap 42 of the tube 16 define an internal chamber that retains the reference fluid 38. A salt bridge 44 separates the reference fluid 38 from the test fluid 32 in the test chamber 30.

The reference fluid 38 provides a known electrochemical potential used as a base or background potential when, for example, applying an electric potential to a test material within the cell 10. The reference fluid 38 may be a salt solution that includes, for example, silver chloride, potassium chloride, or silver nitrate. The salt bridge 44 provides a physical barrier between the reference fluid 38 of the tube 16 and the test fluid 32 of the internal test chamber 30 while allowing electron migration between the reference fluid 38 and the test fluid 32. The salt bridge 44 may include the same salt that is used in the reference fluid 38. The reference fluid 38 and the salt bridge 44 may be conventional in nature.

The conductive element 36 may be silver or platinum wire or foil extending from a location within the tube 16 proximate the salt bridge 44 through the end cap 42 to provide means for placing an external apparatus, such as a potentiostat, in electrical communication with the reference fluid 38. Thus, the conductive element 36 is in electrical communication with the reference fluid 38 but does not contact the salt bridge 44.

A first end of the electrode tube 16 attaches to or is integral with the cell body 12 and a second end of the electrode tube 16 (including the end cap 42) extends generally upwardly and outwardly from the cell body 12. A diameter of the tube 16 may be within the range of from about 0.5 cm to about 1.5 cm or within the range of from about 0.7 cm to about 1.3 cm. More particularly, the diameter of the tube 16 may be about 0.85 cm, about 0.90 cm, or about 0.95 cm. A length of the tube 16 may be within the range of from about 1.0 cm to about 5.0 cm or within the range of from about 2.0 cm to about 4.0 cm. More particularly, the length of the tube 16 may be about 2.5 cm, about 3.0 cm, or about 3.5 cm.

The second electrode tube 18 is defined by a tubular wall 46 that houses a working electrode 48 including, for example, a wire 50 encapsulated in electrically insulating material 52 extending from an outside of the tube 18, through an end cap 54, to a test material 56. The test material 56 may be a specimen of any material that is the target of the analysis or test and may be, for example, a piece of metal of the kind used in a pipeline or a holding tank. The test material 56 is electrically and physically connected to the wire 50 such that the test material 56 may be inserted into the test chamber 30 by inserting the material 56 and the wire 50 through a mouth of the second electrode tube 18.

A first end of the electrode tube 18 attaches to or is integral with the cell body 12 and a second end of the electrode tube 18 extends generally upwardly and outwardly from the cell body 12. A diameter of the tube 18 may be within the range of from about 0.5 cm to about 2.0 cm or within the range of from about 1.0 cm to about 1.5 cm. More particularly, the diameter of the tube 18 may be about 1.2 cm, about 1.3 cm, or about 1.4 cm. A length of the tube 18 may be within the range of from about 1.0 cm to about 5.0 cm or within the range of from about 2.0 cm to about 4.0 cm. More particularly, the length of the tube 18 may be about 2.5 cm, about 3.0 cm, or about 3.5 cm.

The test material 56 is preferably planar and may present substantially any shape, including, for example, a rectangular or circular shape. If the material 56 is rectangular, a length and a width of the material 56 may each be within the range of from about 1.0 mm to about 15.0 mm or within the range of from about 2.0 mm to about 14.0 mm. More particularly, the length and the width of the material 56 may each be about 9.5 mm, about 10.0 mm, or about 10.5 mm. A depth or thickness of the material 56 may be within the range of from about 0.5 mm to about 5.0 mm or within the range of from about 0.6 mm to about 4.5 mm. More particularly, the thickness of the material 56 may be about 2.5 mm, about 3.0 mm, or about 3.5 mm.

The third electrode tube 20 houses a counter electrode including a conductive element 58. An outer tubular wall 60 of the tube 20 holds an electrically insulating retaining material 62. The retaining material 62 includes an axial through-hole that receives and supports the conductive element 58. The conductive element 58 may include a platinum wire that extends from an outside of the tube 20 into the test chamber 30 and in contact with the test fluid 32.

A diameter of the tube 20 may be within the range of from about 0.5 cm to about 1.5 cm or within the range of from about 0.7 cm to about 1.3 cm. More particularly, the diameter of the tube 14 may be about 0.85 cm, about 0.90 cm, or about 0.95 cm. A length of the tube 16 may be within the range of from about 1.0 cm to about 5.0 cm or within the range of from about 2.0 cm to about 4.0 cm. More particularly, the length of the tube 16 may be about 2.5 cm, about 3.0 cm, or about 3.5 cm.

Portions of the test material 56 may be substantially entirely coated with an electrically and chemically insulating material such that only a face 64 of the test material 56 is exposed to, and in contact with, the test fluid 32. Thus, a face opposite the lice 64, as well as various sides or edges, may be coated with the electrically insulating material. Exposing only the face 64 to the test fluid 32 facilitates determining with precision the total amount of surface area of the test material 56 exposed to the test fluid 32, which may be helpful or required in various spectroscopy analyses.

The first electrode tube 16 and the second electrode tube 18 may be radially separated by a first angle a, and the second electrode tube 18 and the third electrode tube 20 may be radially separated by a second angel b. The first angle a and the second angle b may each be within the range of from about 10° to about 170° or from about 30° to about 150°. More particularly, the first angle a and the second angle b may each be about 60°, about 70°, or about 80°. As explained above, each of the tubes 16,18,20 extends upwardly and outwardly relative to the body 12 of the cell 10. An upward angle c of each of the tubes 16,18,20 relative to the body 12 may be within the range of from about 10° to about 80° or within the range of from about 30° to about 70°. More particularly, the upward angle of each of the tubes 16,18,20 may be about 40°, about 45°, or about 50°.

Figure 7:
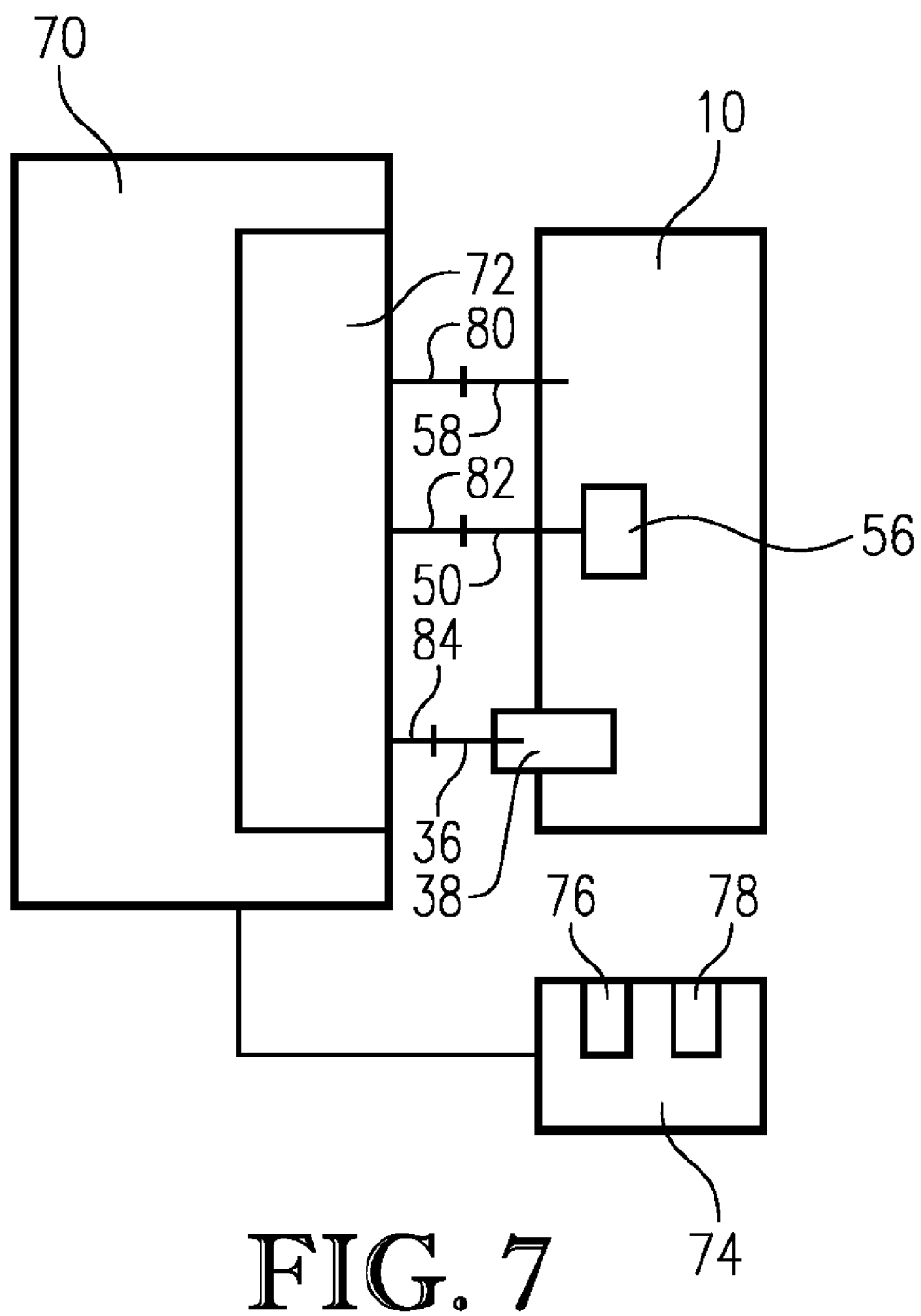
FIG. 7 is a schematic diagram of a spectroscopy system including the cell of FIG. 1 and a spectroscopy instrument.

The cell 10 may be used in spectroscopy analysis, such as surface enhanced Raman spectroscopy. A spectroscopy instrument 70 including a potentiostat 72 may be used with the cell 10 to perform the analyses as illustrated in the schematic diagram of FIG. 7. The potentiostat 72 is connected to the conductive elements 36, 50, and 58. An optical component 74, including a monochromatic light source 76, such as a laser, and an optical sensor 78, is positioned relative to the cell 10 to be generally in register with the window 14 so that light emitted from the light source 76 strikes the test material 56 and is reflected back toward the optical component 74 according to principles of spectroscopy.

The cell 10 is first positioned relative to the light source 76 so that light generated by the light source 76 is reflected by the test material 50 and focused on the light sensor 78. The step of positioning the light source 76 and the cell 10 relative to one another may take a few minutes. This presents a substantial advantage to the conventional methods of preparing a spectroscopy system which include manually moving emitters and sensors and could take hours to complete.

When the cell 10 is aligned with the optical component 74, the potentiostat 72 is electrically connected to the conductive elements 36,50,58. The instrument 70 measures the reference voltage on the conductive element 36 of the reference electrode and applies an electric potential to the test material 56 by applying an electric potential across the conductive element 50 of the working electrode and the conductive element 58 of the counter electrode. The precise voltage applied across the working and counter electrodes may vary from one application to another.

According to an exemplary application, an electric potential of 1200 mV is applies across the working and counter electrodes such that the working electrode is at approximately the same potential as the reference electrode, and a potential of −1200 mV is applied to the counter electrode relative to the working electrode. A SERS spectrum is captured at each of several pre-determined intervals by exposing the test material 56 to light generated by the light source 76, detecting the light reflected from the test material 56 with the optical sensor 78, and analyzing the light detected by the optical sensor 78 to gather information about the test material 56. By way of example, a new SERS spectrum may be captured every onehundred seconds wherein the potential across the working and counter electrodes is increased by 1.0 mV/second until the potential across the conductive elements 50 and 58 is −300 mV.

The present technology can be used to generate SERS spectra using relatively low-power optics. For example, the light source 76 may be a laser emitter operable to generate laser light at a power of between 30 mW and 80 mW.

Although the invention has been described with reference to the embodiments illustrated in the attached drawing figures, it is noted that equivalents may be employed and substitutions made herein without departing from the scope of the invention as recited in the claims. For example, the particular form or function of the various attachment elements is not important to the present technology, and the attachment elements may present alternative shapes and sizes with equally-preferred results.

As used herein, the terms "a," "an," "the," and "said" means one or more.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise," provided below.

As used herein, the terms "having," "has," and "have" have the same open-ended meaning as "comprising," "comprises," and "comprise," provided above As used herein, the terms "including," "includes," and "include" have the same open-ended meaning as "comprising," "comprises," and "comprise," provided above.

As used herein, a "conductor," "conductive element," or "conductive material" is a material with an electrical resistivity of less than about $1 \times 10^{-3}$ Ωm and more preferably less than about $1 \times 10^{-5}$ Ωm.

As used herein, an "insulator," "insulating element," or "insulating material" is a material with an electrical resistivity of more than about 100 Ωm and more preferably more than about $1 \times 10^{3}$ Ωm.

Having thus described various embodiments of the invention, what is claimed as new and desired to be protected by Letters Patent includes the following:

1. A test cell comprising:
    a test chamber at least partially enclosed by a wall, said wall including a window;
    a test fluid within said test chamber;
    a test material within said test chamber, at least a portion of said test material in contact with said test fluid, and at least a portion of said test material in optical register with said window;
    a first conductive element in electrical communication with said test fluid and separated from said test material by a space, said first conductive element extending to an outside of said cell;
    a second conductive element in electrical communication with said test material and extending to said outside of said cell; and
    an electrode chamber containing an electric reference fluid, wherein said electrode chamber is arranged for electron migration between said test fluid in said test chamber and said reference fluid in said electrode chamber.

2. The cell as set forth in claim 1, wherein said window includes a transparent material with a thickness of between 0.1 mm and 0.3 mm.

3. The cell as set forth in claim 1, further comprising a salt bridge separating said electrode chamber from said test chamber.

4. The cell as set forth in claim 3, further comprising a third conductive element in electrical communication with said reference fluid and extending to said outside of said cell.

5. The cell as set forth in claim 1, wherein said window is part of a recessed portion of said wall.

6. The cell as set forth in claim 1, said test chamber presenting a generally cylindrical shape with a diameter within the range of from 2.0 cm to 10.0 cm.

7. The cell as set forth in claim 1, said test material including an electrically insulating coating covering all of said test material except for one face of the test material.

8. The cell as set forth in claim 1, said test chamber having a volume from 20 cm$^3$ to 60 cm$^3$.

9. A test cell with an internal test chamber separated from an outside of said cell by a wall, said cell comprising:
    a top planar segment of said wall including a substantially transparent portion;
    a test fluid within said test chamber;
    a test material within said test chamber and immersed in said test fluid, said test material partially coated with an electrically insulating material such that only a single exposed face of said test material is in contact with said test fluid, wherein said exposed face is in optical register with said substantially transparent portion of said wall;
    a first conductive element in electrical communication with said test fluid and extending to said outside of said cell;
    a second conductive element with a first end in contact with said test fluid and a second end extending to said outside of said cell, wherein said first end of said second conductive element is separated from said test material by a space, wherein said second conductive element is covered with an electrically insulating material preventing the second conductive element from contacting said test fluid; and
    a third conductive element in electrical communication with said test material and extending to said outside of said cell.

10. The cell as set forth in claim 9, further comprising a first electrode chamber containing an electrical reference fluid, wherein said electrode chamber is arranged for electron migration between said test fluid in said test chamber and said reference fluid in said electrode chamber.

11. The cell as set forth in claim 10, wherein said first electrode chamber includes a salt bridge separating said reference fluid from said internal test chamber.

12. The cell as set forth in claim 11, wherein said third conductive element has its first end in contact with said reference fluid and a second end extending to said outside of said cell.

13. The cell as set forth in claim 9, said wall including a peripheral circular portion with a diameter that is within the range of from 2.0 cm to 10.0 cm.

14. The cell as set forth in claim 9, said wall presenting a thickness within the range of from 0.3 mm to 1.7 mm.

15. The cell as set forth in claim 9, wherein said substantially transparent portion of said wall includes a sheet of material secured to said wall with an adhesive.

16. The cell as set forth in claim 15, said sheet of transparent material having a thickness within the range of from 0.1 mm to 0.3 mm.

17. The cell as set forth in claim 9, wherein said internal chamber of said cell has a volume of from 20 cm$^3$ to 60 cm$^3$.

18. A method of performing a spectroscopy analysis, said method comprising:

adding a test fluid to an internal chamber of a cell;

placing a test material in said cell such that said test material is at least partially in contact with said test fluid;

attaching a first conductive element to said test material such that the first conductive element extends outside of said cell, wherein said first conductive element and said test material are coated with an electrical insulating material such that only a single face of said test material is exposed to said test fluid;

aligning a substantially transparent portion of said cell with an optical component of a spectroscopy instrument, said optical component including a light emitter;

applying an electric potential between said test material and a second conductive element, said second conductive element being in contact with said test fluid and separated from said test material by a space;

providing an electrochemical potential to said test fluid from a third conductive element through a reference fluid;

performing said spectroscopy analysis on said test material by exposing said test material to light generated by said emitter and capturing light reflected from said test material using said optical component.

19. The method as set forth in claim 18, further comprising applying an electric potential to said test material by applying an electric potential between said test material and an electrode in contact with said test fluid and separated from said test material by a space.

20. The method as set forth in claim 18, wherein said step of exposing said test material to light generated by said emitter includes operating a laser light generator at between 30 mW and 80 mW.

21. The method as set forth in claim 18, wherein said internal chamber presents a volume of from 20 cm$^3$ to 60 cm$^3$.

22. The method as set forth in claim 18, further comprising coating said test material with an electrical insulator such that only a single face of said test material is exposed to said test fluid.

23. A method of performing a spectroscopy analysis, said method comprising:

adding a test fluid to an internal chamber of a cell;

placing a test material in said cell such that said test material is submersed in said test fluid, said test material including a first conductive element extending to an outside of said cell, wherein said first conductive element and said test material are coated with an electrical insulating material such that only a single face of said test material is exposed to said test fluid;

aligning said test material with a substantially transparent portion of said cell;

aligning said substantially transparent portion of said cell with an optical component of a spectroscopy instrument, said optical component including a light emitter and a light sensor;

applying an electric potential between said test material and a second conductive element, said second conductive element being in contact with said test fluid and separated from said test material by a space;

providing an electrochemical potential to said test fluid from a third conductive element through a reference fluid in an electrode chamber; and performing said spectroscopy analysis on said test material by exposing said test material to light generated by said emitter and capturing light reflected from said test material using said optical component.

24. The method as set forth in claim 23, wherein said internal chamber of said cell has a volume of from 20 cm$^3$ to 60 cm$^3$.

* * * * *